US011453884B2

(12) United States Patent
Chappell et al.

(10) Patent No.: US 11,453,884 B2
(45) Date of Patent: *Sep. 27, 2022

(54) METHOD AND SYSTEM FOR TERPENE PRODUCTION PLATFORMS IN YEAST

(71) Applicant: University of Kentucky Research Foundation, Lexington, KY (US)

(72) Inventors: Joe Chappell, Lexington, KY (US); Xun Zhuang, Lexington, KY (US); Shuiqin Wu, San Diego, CA (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 87 days.

This patent is subject to a terminal disclaimer.

(21) Appl. No.: 16/990,802

(22) Filed: Aug. 11, 2020

(65) Prior Publication Data

US 2021/0071185 A1 Mar. 11, 2021

Related U.S. Application Data

(63) Continuation of application No. 14/092,496, filed on Nov. 27, 2013, now Pat. No. 10,738,328.

(60) Provisional application No. 61/730,412, filed on Nov. 27, 2012.

(51) Int. Cl.
*C12N 15/81* (2006.01)
*C12N 15/01* (2006.01)
*C12P 5/00* (2006.01)

(52) U.S. Cl.
CPC ............. *C12N 15/81* (2013.01); *C12N 15/01* (2013.01); *C12P 5/007* (2013.01)

(58) Field of Classification Search
CPC .......... C12N 15/81; C12N 15/01; C12P 5/007
See application file for complete search history.

(56) References Cited

U.S. PATENT DOCUMENTS

| | | | |
|---|---|---|---|
| 6,531,303 B1 | 3/2003 | Millis et al. | |
| 6,689,593 B2 * | 2/2004 | Millis .................. | C07C 403/08 435/155 |
| 6,828,092 B1 | 12/2004 | Dixon et al. | |
| 7,172,886 B2 | 2/2007 | Keasling et al. | |
| 7,927,862 B2 | 4/2011 | Millis et al. | |
| 7,985,567 B2 | 7/2011 | Chou et al. | |
| 8,114,645 B2 | 2/2012 | Pitera et al. | |
| 10,597,665 B1 * | 3/2020 | Chappell ................ | C12N 15/01 |
| 10,738,328 B1 * | 8/2020 | Chappell ................ | C12N 9/88 |
| 2004/0072323 A1 | 4/2004 | Matsuda et al. | |
| 2007/0015237 A1 | 1/2007 | Bailey et al. | |
| 2008/0020438 A1 | 1/2008 | Matsuda et al. | |
| 2009/0324800 A1 | 12/2009 | Bailey et al. | |
| 2011/0021843 A1 | 1/2011 | Bailey et al. | |
| 2011/0039299 A1 | 2/2011 | Bailey et al. | |
| 2012/0149886 A1 | 6/2012 | Bailey et al. | |

OTHER PUBLICATIONS

Kim, Tae-Dong, et al., "Expression and Functional Characterization of Three Squalene Synthase Genes Associated with Saponin Biosynthesis in Panas ginseng", Plant Cell Physiol., (2010) 52(1): 125-137.

Asadollahi MA, Maury J, Moller K, Nielsen KF, Schalk M, Clark A, Nielsen J (2008) Production of plant sesquiterpenes in *Saccharomyces cerevisiae*: Effect of ERG9 repression on sesquiterpene biosynthesis. Biotechnology and Bioengineering 99: 666-677.

Asadollahi MA, Maury J, Schalk M, Clark A, Nielsen J (2010) Enhancement of farnesyl diphosphate pool as direct precursor of sesquiterpenes through metabolic engineering of the mevalonate pathway in *Saccharomyces cerevisiae*. Biotechnology and Bioengineering 106: 86-96.

Bedoukian PE (1983) Perfumery and flavour materials. Perfumer & Flavorist 8: 1, 3-6.

Bergstrom JD, Dufresne C, Bills GF, Nallinomstead M, Byrne K (1995) Discovery, biosynthesis, and mechanism of action of the zaragozic acids ¬potent inhibitors of squalene synthase. Annual Review of Microbiology 49: 607-639.

Bourot S, Karst F (1995) Isolation and characterization of the *saccharomycescerevisiae* sut1 gene involved in sterol uptake. Gene 165: 97-102 Buckingham J (2003) Dictionary of Natural Products. Chapman & Hall/CRC Chemical Database.

Bhilwade HN, Tatewaki N, Nishida H, Konishi T (2010) Squalene as novel food factor. Current Pharmaceutical Biotechnology 11: 875-880.

Casida JE (2009) Pest toxicology: The primary mechanisms of pesticide action. Chemical Research in Toxicology 22: 609-619.

Fischer MJC, Meyer S, Claude! P, Bergdoll M, Karst F (2011) Metabolic engineering of monoterpene synthesis in yeast. Biotechnology and Bioengineering 108: 1883-1892.

Huang Z-R, Lin Y-K, Fang J-Y (2009) Biological and pharmacological activities of squalene and related compounds: potential uses in cosmetic dermatology. Molecules 14: 540-554.

Janke C, Magiera MM, Rathfelder N, Taxis C, Reber 5, Maekawa H, Moreno-Borchart A, Doenges G, Schwob E, Schiebel E, Knop M (2004) A versatile toolbox for PCR-based tagging of yeast genes: new fluorescent proteins, more markers and promoter substitution cassettes. Yeast 21: 947-962.

Keasling J (2009) Synthetic biology in pursuit of inexpensive, effective, anti-malarial drugs. Biosocieties 4: 275-282.

Kirby J, Romanini DW, Paradise EM, Keasling JD (2008) Engineering triterpene production in *Saccharomyces cerevisiae*-beta-amyrin synthase from Artemisia annua. Febs Journal 275: 1852-1859.

(Continued)

*Primary Examiner* — Mary Maille Lyons
(74) *Attorney, Agent, or Firm* — Stephen J. Weyer, Esq.; Stites & Harbison, PLLC

(57) ABSTRACT

A method is provided for producing modified mutant yeast and the resulting yeast that can be used as a platform for terpene production. The method includes chemical mutagenesis to effect ergosterol dependent growth in yeast. Subsequently, these yeast are subjected to an erg9 knockout mutation to thereby produce ergosterol dependent growth/erg9 knockout mutation yeast cell lines. The resulting yeast are well suited for use in the production of terpenes.

1 Claim, 15 Drawing Sheets

Specification includes a Sequence Listing.

(56) References Cited

OTHER PUBLICATIONS

Maertens JA (2004) History of the development of azole derivatives. Clinical Microbiology and Infection 10: 1-10.

Martin VJJ, Pitera DJ, Withers ST, Newman JD, Keasling JD (2003) Engineering a mevalonate pathway in *Escherichia coli* for production of terpenoids. Nature Biotechnology 21: 796-802.

Mathis JR, Back K, Starks C, Noel J, Poulter CD, Chappell J (1997) Pre-steady-state study of recombinant sesquiterpene cyclases. Biochemistry 36: 8340-8348.

Nicolaou KC, Yang Z, Liu JJ, Ueno H, Nantermet PG, Guy RK, Claiborne CF, Renaud J, Couladouros EA, Paulvannan K, Sorensen EJ (1994) Total synthesis of taxol. Nature 367: 630-634.

Reddy LH, Couvreur P (2009) Squalene: A natural triterpene for use in disease management and therapy. Advanced Drug Delivery Reviews 61: 1412¬1426.

Seki H, Ohyama K, Sawai S, Mizutani M, Ohnishi T, Sudo H, Akashi T, Aoki T, Saito K, Muranaka T (2008) Licorice beta-amyrin 11-oxidase, a cytochrome P450 with a key role in the biosynthesis of the triterpene sweetener glycyrrhizin. Proceedings of the National Academy of Sciences of the United States of America 105: 14204-14209.

Shianna KV, Dotson WD, Tove S, Parks LW (2001) Identification of a UPC2 homolog in *Saccharomyces cerevisiae* and its involvement in aerobic sterol uptake. Journal of Bacteriology 183: 830-834.

Silva L, Coutinho A, Fedorov A, Prieto M (2006) Competitive binding of cholesterol and ergosterol to the polyene antibiotic nystatin. A fluorescence study. Biophysical Journal 90: 3625-3631.

Takahashi S, Yeo Y, Greenhagen BT, McMullin T, Song L, Maurina-Brunker J, Rosson R, Noel JP, Chappell J (2007) Metabolic engineering of sesquiterpene metabolism in yeast. Biotechnology and Bioengineering 97: 170-181.

Tu Y (2011) The discovery of artemisinin (qinghaosu) and gifts from Chinese medicine. Nature Medicine 17: 1217-1220.

Wall ME, Wani MC (1995) Paclitaxel—from discovery to clinic. In GICTTOIVDM Georg, ed, Taxane Anticancer Agents: Basic Science and Current Status, vol. 583, pp. 18-30.

Wu SQ, Schalk M, Clark A, Miles RB, Coates R, Chappell J (2006) Redirection of cytosolic or plastidic isoprenoid precursors elevates terpene production in plants. Nature Biotechnology 24: 1441-1447.

Zhang DL, Jennings SM, Robinson GW, Poulter CD (1993) Yeast squalene synthase—expression, purification, and characterization of soluble recombinant enzyme. Archives of Biochemistry and Biophysics 304: 133¬143.

Kavscek et al. 2015 (Yeast as a cell factory: current state and perspectives; Microbial Cell Factories 14:94). (Year: 2015).

Kennedy et al. 1999 (Transcriptional regulation of the squalene synthase gene (ERG9) in the yeast *Saccharomyces cerevisiae*; Biochimica et Biophysica Acta 1445:110-122).

Genetic Nomenclature Guide. 1998. SGD (*Saccharomyces* Genome Database) http://genomewww.stanford.edu/Saccharomyces/.

Grabowska et al. 1998 (Effect of squalene synthase gene disruption on synthesis of polyprenols in *Saccharomyces cerevisiae*; FEBS Letters 434:466-408).

Tarshis et al. 1994 (Crystal Structure of Recombinant Farnesyl Diphosphate Synthase at 2.6 A Resolution; Biochemistry 33:10871-10877).

\* cited by examiner

METHOD AND SYSTEM FOR TERPENE PRODUCTION PLATFORMS IN YEAST

CROSS-REFERENCE TO RELATED APPLICATION

This application is a continuation of U.S. Ser. No. 14/094,496 which issued as U.S. Pat. No. 10,738,328, which in turn claims the benefit of provisional patent application No. 61/730,412, filed Nov. 27, 2012, all herein incorporated by reference.

FIELD OF THE INVENTION

The presently-disclosed subject matter relates to methods for producing or generating modified yeast, and the resulting yeast, and in particular yeast that can be used for various aspects of terpene production. For example, the subject matter relates to methods and systems for building terpene production platforms in yeast which have various introduced mutations. These platforms or cell lines can be further modified, e.g. genetically engineered to produce specific enzymes and/or terpenes.

BACKGROUND OF THE INVENTION

Plants, microorganisms and animals produce a large variety of organic chemical compounds, some of which are used universally for growth and metabolism and others seem to play specialized roles in the life cycle of the organism (Maimone & Baran, 2007). As such, two large classes of natural products are widely recognized. Primary metabolites are those essential for live in all eukaryotic organisms, while specialized metabolites appear to give species specific advantages for occupying distinct environmental niches. The distinctive role specialized metabolites play in an organisms natural history, for example how these metabolites provide protection against microbial challenge, have also not escape attention for their possible utility in a wide range of applications. For example, many of the currently used drugs are derived or inspired from plant-derived specialized chemicals and are commonly referred to as Natural Products (Buchanan et al., 2002). Capturing the chemical and structural diversity of Natural Products has recently been identified as a major objective within the scientific community in large part because of the wide array of applications Natural Products can have and the resulting economical implications.

Terpenes and terpenoids are a large and diverse family of Natural Products with more than 55,000 having been identified (Maimone & Baran, 2007). However, based on the biosynthetic mechanisms responsible for terpenes, chemists have predicted that only a small fraction of all the possible terpene compounds have been discovered (Bouvier et al., 2005). Terpenes are derived from the five carbon isoprene unit with different combinations of the isoprene units generating different classes of the terpene products. The classification and biosynthesis of terpenoids are based on the number of five-carbon units they contain as illustrated in FIG. 1. Monoterpenes (consisting of 10 carbons), sesquiterpenes (15 carbon derivatives), and diterpenes (20 carbon derivatives), arise from the corresponding intermediates geranyl diphosphate (GPP), farnesyl diphosphate (FPP), and geranylgeranyl diphosphate (GGPP). These intermediates in turn arise by the sequential head to tail condensation of C5 units. Higher order terpenes like triterpene (30 carbons) are formed from two farnesyl units condensed head-to-head. Likewise, tetraterpenes (40 carbons) are formed from two geranylgeranyl units condensed head-to-head.

Monoterpenes are well known as the volatile essence of flowers and plants and such mixtures can account for up to 5% of plant dry weight (Buchanan et al., 2002). Menthol and camphor are common monoterpenes found in diverse plant families and whose structural complexity in terms of stereo- and regio-chemistry are emphasized in FIG. 2. Besides providing pleasing fragrances, monoterpenes have been shown to function as signal molecules in defense mechanisms against pathogens (Hick et al., 1999). Hence, monoterpenes have the commercial value as flavors, fragrances, essential oils, and as anticancer and antimicrobial drugs (Burke et al., 1997). Sesquiterpenes (C15) are also found in essential oils, and many sesquiterpenes possess antibiotic activities, prompting suggestions that they are produced by plants as a defense mechanism. Diterpenes (C20) include gibberellins (plant hormones), vitamin A, as well as pharmaceutical important metabolites such as taxol, an exceptional anticancer regent (Barkovich & Liao, 2001). Triterpenes (C30) include the brassinosteroids, phytosterols important for lipid membrane composition, and components of surface waxes, such as oleanolic aid of grapes. Squalene, the major content of shark liver oil, is a linear triterpene and common ingredient in cosmetic products (Buchanan et al., 2002), has special utility as a lubricant for high performance machinery, and is a common adjuvant in many pharmaceutical formulations (Bhilwade et al., 2010, Huang et al., 2009, Reddy & Couvreur, 2009). Tetraterpenes (C40) include carotenoid accessory pigments, like lycopene, the monocyclic gamma-carotene, and the bicyclic alpha- and beta-carotenes, which perform essential for the light reactions of photosynthesis. Longer chain terpenes, so-called polyterpenes, contain more than 8 isoprene units and include examples like ubiquinone and rubber (Buchanan et al., 2002).

There are two pathways for terpene biosynthesis in plant cells. One is the mevalonate pathway pathway (MVA) which is well established and discovered in the 1960s (Bouvier et al., 2005). The other is the mevalonate independent pathway, or more properly referred to as the methylerythritol-phosphate pathway (MEP), which was more recently discovered (Bouvier et al., 2005). The MEP pathway was first discovered in prokaryote cells, and then confirmed to exist in plant cells (Barkovich & Liao, 2001). Interestingly, plants utilize these two pathways to meet different terpene biosynthetic needs. Sesquiterpenes, sterols, triterpenes and oligoterpenes (side chain of dolichols) are synthesized in the cytosol via the MVA pathway, while monoterpenes, diterpenes, teraterpenes, and polyterpenoids are synthesized in chloroplasts via the MEP pathway using pyruvate and glyceraldehydes-3-phosphate as the primary precursors (FIG. 2).

The principal product of the mevalonate pathway is sterols, for example cholesterol in animal cells, stigmasterol and campesterol in plant cells, and ergosterol in fungi, which all play essential roles in establishing the structural integrity of membranes, establishing permeability and fluidity, and also serving as signal compounds in cellular communication (Buchanan et al., 2002). In *Saccharomyces cerevisiae*, only the mevalonate pathway is known to operate and no components of the MEP pathway have been found (Maury et al., 2005). FIG. 3 shows the intermediates and the related genes involved in the yeast mevalonate pathway (Maury et al., 2005). Two molecules of acetyl-CoA are condensed by acetoacetyl-CoA thiolase, which is encoded by ERG10, to synthesize acetoacetyl-CoA. A second condensation reaction between acetoacetyl-CoA and acetyl-CoA is then catalyzed by HMG-CoA synthase encoded by ERG13 to yield 3-hydroxy-3methyglutaryl-CoA (HMG-CoA).

TABLE 1

Biological activities and commercial applications of typical terpenoids

| Class | Biologic activities | Commercial applications | Examples |
|---|---|---|---|
| Monoterpenoids | Signal molecules and used as defense mechanisms against pathogens | Flavors, fragrances, cleaning products, anticancer, antibacterial, antioxidant, essential oil, biofuel | Limonene, menthol, camphor, linalool |
| Sesquiterpenoids | Antibiotic, antitumor, antiviral, immuno-suppressive, and hormonal activities, defensive agents or pheromones | Flavors, fragrances, pharmaceuticals (antibacterial, antifungal), insecticides, biofuels | Nootkatone, artemisinin, patchoulol, nerolidol, farnesol, capsidol, farnesene, bisabolene |
| Diterpenoids | Hormonal activities, growth regulator, antitumor, antimicrobial and anti-inflammatory properties | Anticancer agents, feedstock for industrial chemical applications | Gibberellins, phytol, taxol, kaurene, abietadiene, kaurenoic acid, abietic acid |
| Triterpenoids | Membrane component, steroid hormones | Biologic markers, biofuel, skin moisturizers in cosmetics, immunologic adjuvant in vaccines. | Sterols, hopanoids, squalene, botryococcene. |
| Tetraterpenoids | Antioxidants, photosynthetic components, pigments, and nutritional elements (vitamins) | Food additives, colorants, antioxidants | Lycopene, beta-carotene |

HMG-CoA is reduced by HMG-CoA reductase to yield mevalonate. This reaction is catalyzed by HMG-CoA reductase, which is encoded by 2 separate loci in yeast. Both loci appear to compensate for a knockout loss of the other gene. The C5 position of mevalonate is phosphorylated by mevalonate kinase, encoded by ERG12. Then a second kinase, phosphomevalonate kinase, encoded by ERG8, catalyzes the successive phosphorylation to yield diphosphomevalonate. In the next step the diphosphomevalonate is converted into IPP (isopentenyl diphosphate) by mevalonate diphosphate decarboxylase, encoded by ERG19. IPP isomerase, encoded by IDI1 converts IPP into DMAPP (dimethylallyl diphosphate). The condensation of the C5 building blocks of IPP and DMAPP into FPP is catalyzed by FPP synthase, which is encoded by ERG20. FPP can then be used as substrate for sterol and other isoprenoid biosynthetic needs.

Recent studies have discovered that FPP is also available in yeast mitochondria, as evidenced by increasing novel sesquiterpene production three-times by targeting a sesquiterpene synthase to the mitochondria compartment compared with targeting this same enzyme to the cytosol (Farhi et al., 2011). The origin of FPP in mitochondria could be the IPP and DMAPP arising in cytosol being imported and converted in the mitochondria to FPP. Alternatively, a hypothetical leucine metabolism model for the formation of terpene in *S. cerevisiae* is also a possibility. The leucine catabolism pathway (MCC pathway) is known to occur in the mitochondria of other eukaryotic mammal and plant cells (Anderson et al., 1998), in mitochondria leucine metabolite to form 3-Hydroxy-3-methylglutaryl-CoA, which can be catalyzed by HMGR to produce mevalonic acid, and then produce IPP and DMAPP through MVA pathway as shown in FIG. 4 (Carrau et al., 2005). Interestingly, a yeast line engineered with a chimeric diterpene synthase targeted to the cytoplasm along with prenyltransferases streamlined for GGPP biosynthesis, yielded 2-3 times more diterpene when the expression vector also provided a leu2 auxotrophic selection marker gene. The interpretation provided by the authors was that the extra leucine produced by the auxotrophic selection marker gene provided another source for IPP via the leucine catabolic pathway (FIG. 4). (Zhou et al., 2012).

Prenyltransferases generate allylic diphosphate esters GPP, FPP, and GGPP. These compounds can undergo a variety of reactions, which include cyclization reactions catalyzed by terpene synthases, yielding diverse terpenes based on regio- and stereo-chemical constraints built into the reactions. Prenyltransferases and terpene synthases utilize electrophilic reaction mechanisms to mediate the catalytic reactions (Ohnuma et al., 1996) and typically share a conserved aspartate-rich DDXXD motif thought important for the initial substrate binding and metal-dependent ionization step leading to the first reaction carbocation intermediates. In the prenyltranferase reactions, the allylic diphosphate ester can be ionized to form a carbocation, then condensed with a second IPP in another round of elongation.

Terpenes are a very large class of structurally diverse compounds made by organisms in all kingdoms of life. The terpenes from plants are perhaps the most extensively described as evident by well over 100,000 different terpenes reported in the literature (Buckingham, 2003). Terpenes are also widely recognized for their diverse utility and applications. For example, taxol, a diterpene widely recognized for its application as a chemotherapeutic agent, was first isolated from the bark and needles of several *Taxus* plant species (Wall and Wani, 1995). Likewise, Artemisinin, a sesquiterpene isolated from the plant *Artemisia annua*, has been developed as a key pharmacological agent for the control of malaria (Tu, 2011). Patchouli, another sesquiterpene, is a popular aromatic found in colognes, perfumes and many other household cleaning products (Wu et al., 2006). Menthol is a monoterpene obtained from mint family plants and is a popular ingredient in many foods and consumer products (Bedoukian, 1983). Triterpenes such as squalene, obtained from various plant sources and the livers of deep sea sharks, have utility as a nutraceutical product, is used extensively in many types of cosmetics, has special utility as a lubricant for high performance machinery, and is a common adjuvant in many pharmaceutical formulations (Huang et al., 2009; Reddy and Couvreur, 2009; Bhilwade et al., 2010).

Terpenes are, however, generally made by plants and microbes in small amounts and components of complex mixtures that vary with growth and environmental conditions, making it difficult to reproducibly obtain large amounts of any one terpene constituent (Wu et al., 2006). Chemical synthesis of terpenes is often costly and inefficient (Nicolaou et al., 1994). Chemical synthesis also suffers from generating enantiomeric mixtures, which adds other complications if one particular stereochemical form of a terpene is desired. Given such difficulties, there are many on-going efforts to create robust, reliable and efficient biological systems for the production of distinct classes of terpenes, and more so for the generation of stereochemically pure forms of terpenes (Martin et al., 2003; Wu et al., 2006; Takahashi et al., 2007; Asadollahi et al., 2008; Kirby et al., 2008; Seki et al., 2008; Keasling, 2009; Asadollahi et al., 2010; Fischer et al., 2011).

SUMMARY OF THE INVENTION

The presently disclosed subject matter relates to methods for producing modified yeast cell lines to produce "platforms" in yeast and the resulting modified yeast or platforms. The production platforms can be further modified to produce specific terpenes such as monoterpenes, diterpenes and/or triterpenes.

Referring generally to one specific technique for producing modified yeast cell lines in accordance with the present disclosure, a series of steps are used to generate genetically modified yeast. The steps include chemical mutagenesis followed by growth on a semi-solid medium containing nystatin, squalestatin and cholesterol. Individual yeast colonies growing on the semi-solid medium are screened for ergosterol dependent growth and then subject to an erg9 (squalene synthase) knockout mutation. Yeast having the erg9 knockout mutation are confirmed via having ergosterol dependent growth. Accordingly, the present technique combines chemical mutagenesis to generate ergosterol dependent yeast lines followed by generating erg9-knockout mutations in the ergosterol dependent yeast lines. One unique aspect of this method includes the use of squalestatin to screen chemically induced mutations in yeast which show ergosterol dependent growth.

The present invention, or one form thereof relates to a method for generating terpene producing cell lines. The method includes combining yeast with a chemical mutagenesis agent to induce mutations in the yeast to generate chemically mutated yeast. The chemically mutated yeast is selected by growth in the presence of nystatin, squalestatin and cholesterol, followed by selecting for ergosterol dependent growth. The ergosterol dependent growth yeast are subjected to an erg9 knockout mutation to thereby produce ergosterol dependent growth/erg9 knockout mutation yeast cell lines. In one further specific form of the present method, the ergosterol dependent growth yeast are subject to an erg9 knockout mutation by inserting a foreign gene sequence into the ergosterol dependent growth yeast at a location of erg9 to effect gene replacement, thereby generating the erg9 knockout mutation. In an alternative further method, the foreign gene sequence can confer chemical resistance to the ergosterol dependent growth/erg9 knockout mutation yeast cell line.

The present invention, in another form thereof, relates to a non naturally occurring yeast which has ergosterol dependent growth and is erg9$^-$.

The present invention, in yet another form thereof relates to ergosterol dependent growth/erg9 knockout mutation yeast cell lines produced by the aforementioned method.

The present method and cell lines provide advantages over wild type and other prior known modified yeast cell lines. For example, the present method and resulting cell lines are especially beneficial for use as terpene platforms for further modification to specifically produce desired terpenes which include monodie and triterpenes.

The yeast lines generated in accordance with this disclosure have utility for the production of diverse classes of terpenes including monoterpenes, sesquiterpenes, diterpenes and triterpenes.

DETAILED DESCRIPTION

The present method and modified yeast will now be described with reference to the figures and exemplary experiments, examples and methods. The figures, experiments and examples are merely to provide a more thorough understanding of the present method and modified yeast. However, other methods and generated yeast can be envisioned consistent with the scope and spirit of the present disclosure.

Figure 1:
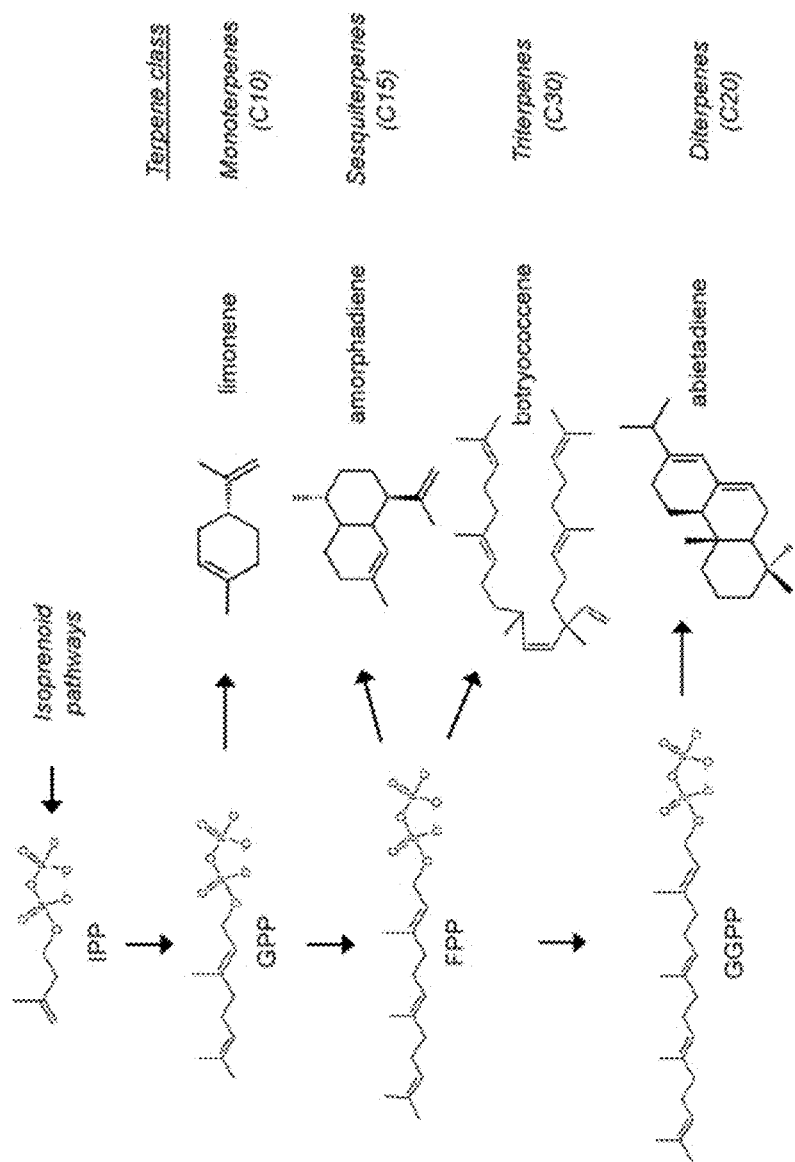
FIG. 1 shows biosynthesis of terpenes from natural sources, which often occurs as diverse mixtures with varying compositions in limited amounts due to environmental influences, in which production of single specific terpenes in genetically engineered yeast would alleviate such variability and yield highly valued, single entity compounds.
Figure 2:
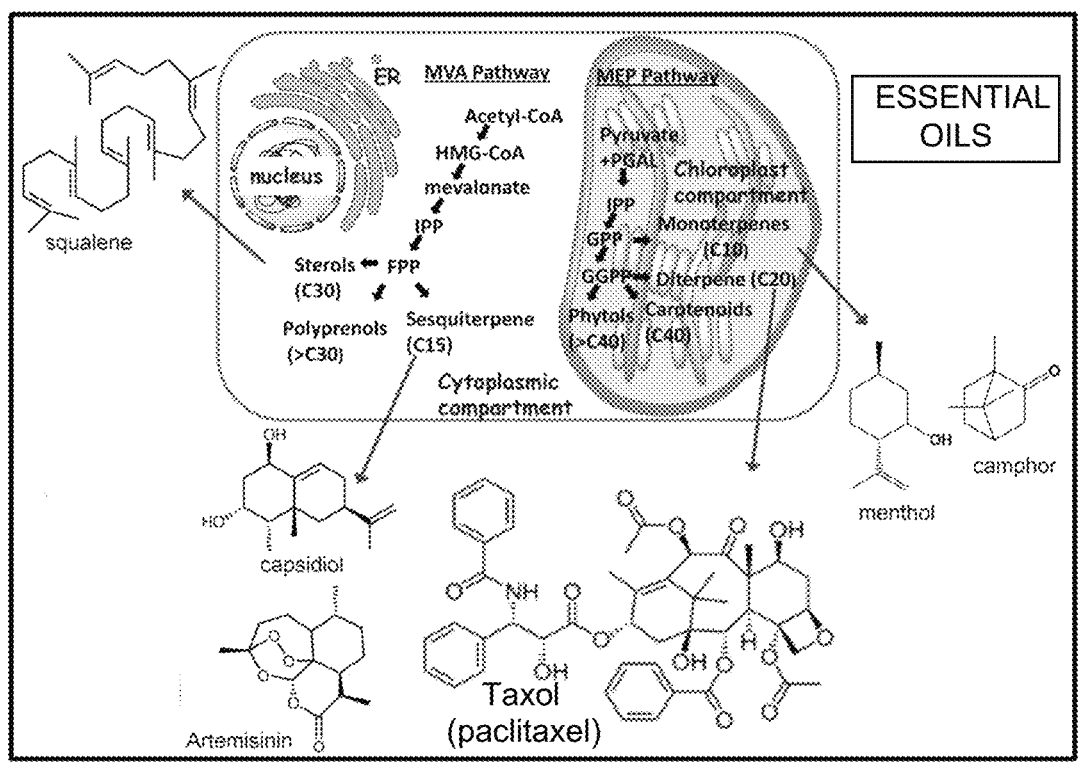
FIG. 2 is schematic outline of two terpene biosynthetic pathways that operate in plants (the MVA and MEP pathways), their intracellular locations, and examples of the chemical compounds derived from each.
Figure 3:
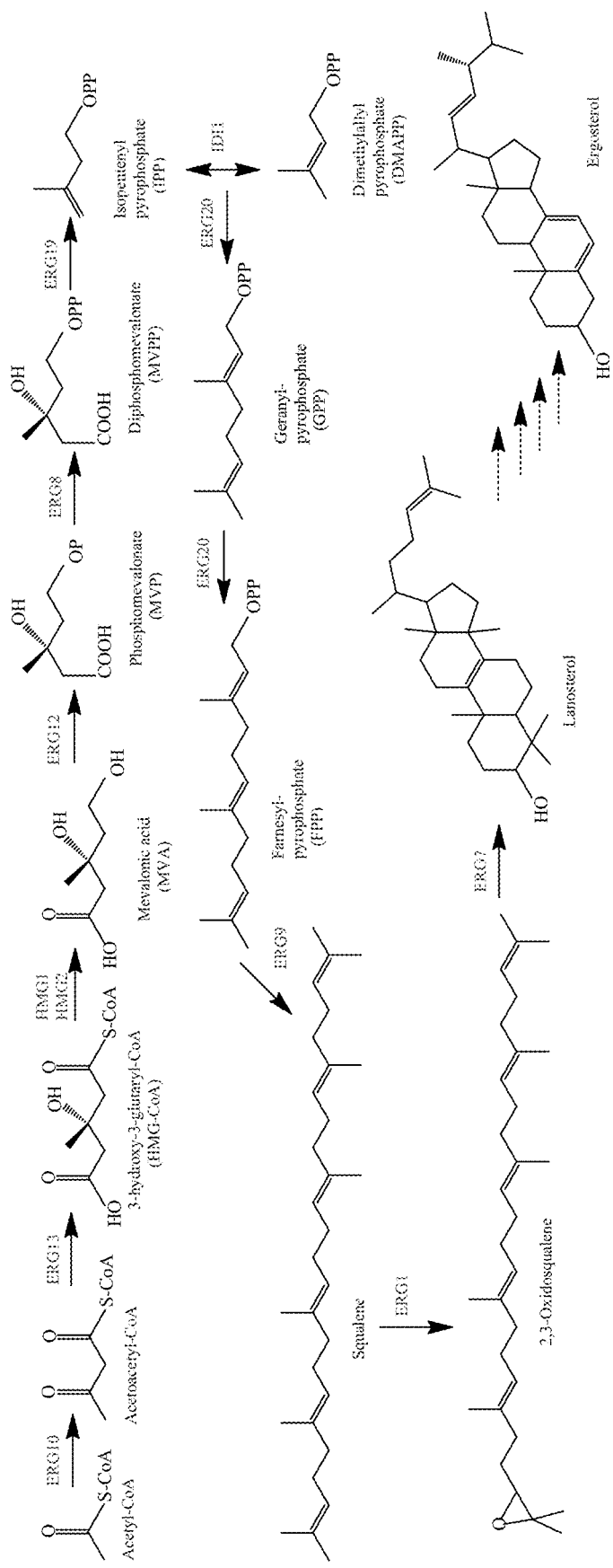
FIG. 3 illustrates mevalonate pathway for ergosterol biosynthesis in yeast (*S. cerevisiae*).
Figure 4:
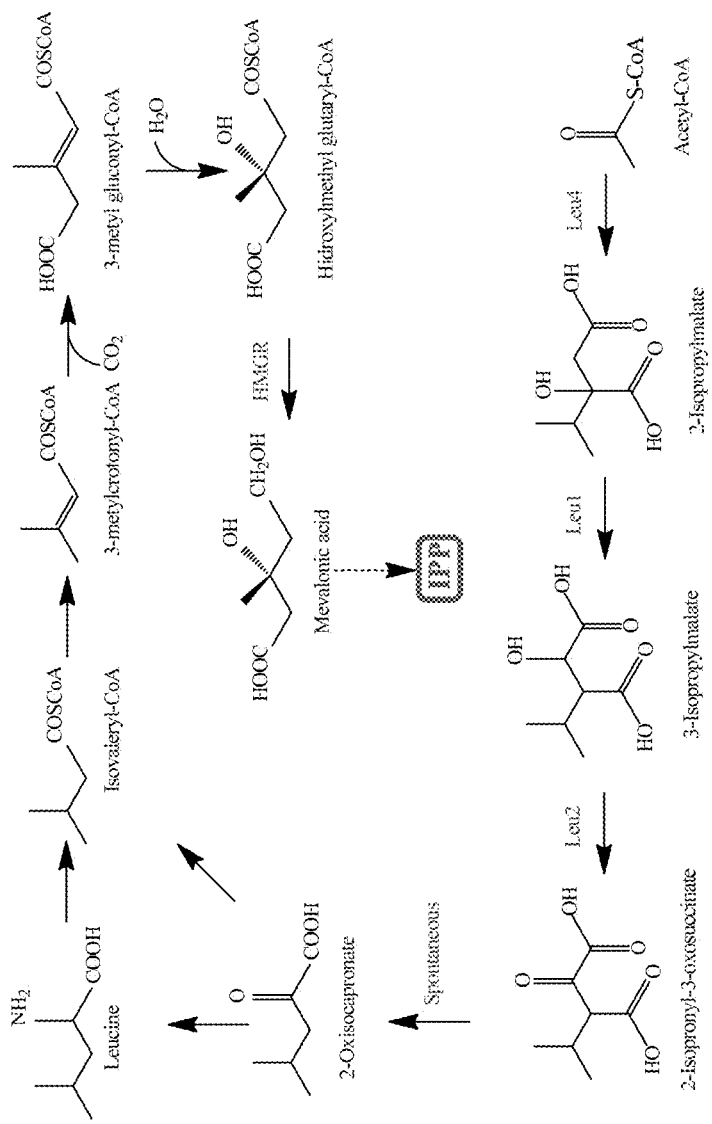
FIG. 4 illustrates an alternative metabolic pathway for HMG-CoA formation pathway through leucine catabolism pathway.
Figure 5:
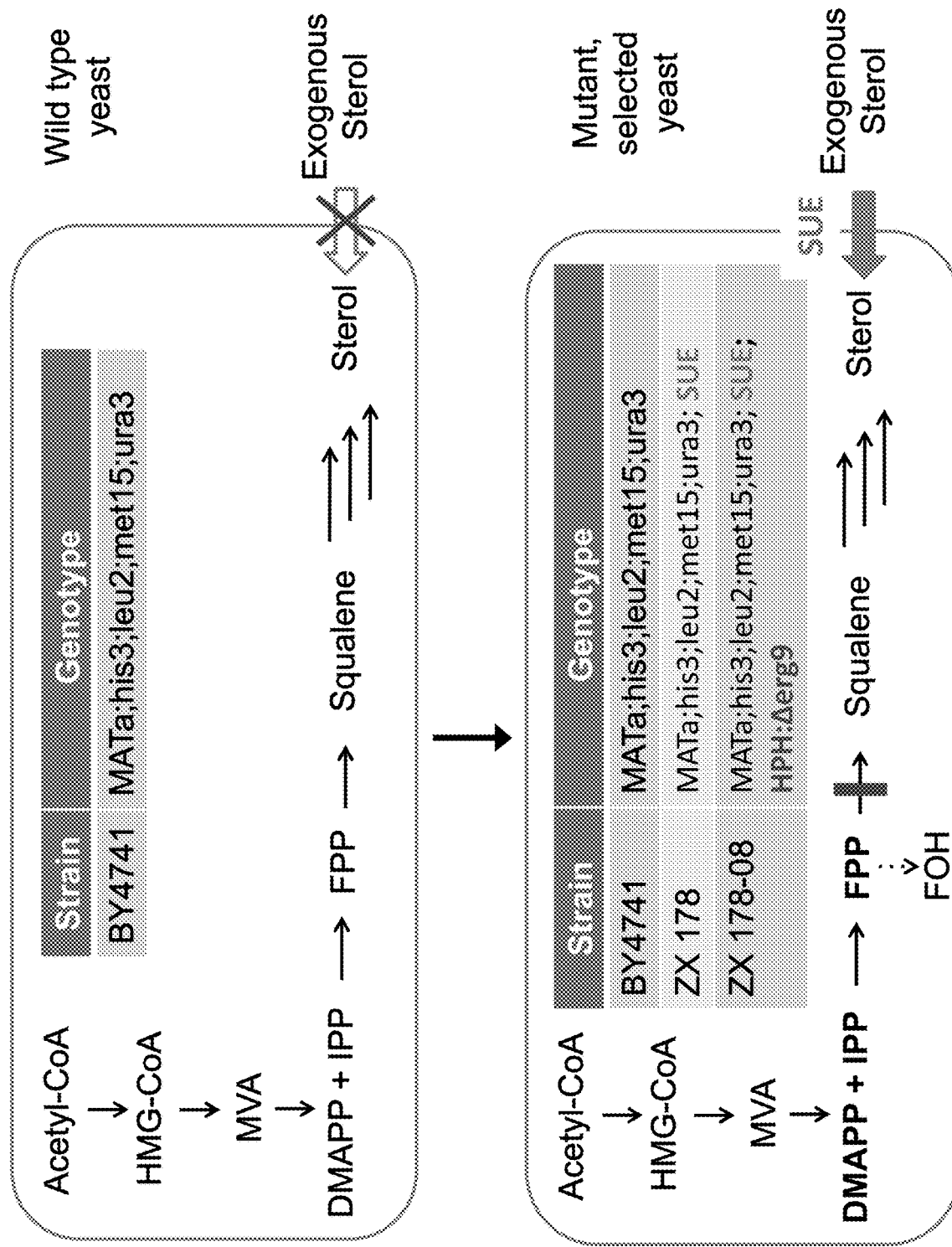
FIG. 5 illustrates the metabolic pathway in modified yeast strains in accordance with the present invention.

FIG. 5 illustrates one approach used to generate yeast cell lines in accordance with the present disclosure. The approach of FIG. 5 outlines a method for generating yeast cell lines that provide for robust biosynthesis or precursors that can be utilized in the production of many difference classes of terpenes. The strategy takes advantage of the native mevalonate (MVA) pathway that operates normally in yeast for the biosynthesis of ergosterol, the dominant sterol found in yeast. Ergosterol is the main product of the yeast mevalonate pathway, is an important membrane component, and is essential for yeast growth. If the ergosterol biosynthetic pathway is blocked or inhibited, yeast die. In fact, this is the basis for many pharmacological drugs to control fungal infections in man (Maertens, 2004) and agricultural chemicals to control fungal infection in plants (Casida, 2009). To further complicate matters, wild type yeast can take up exogenously supplied sterol from their environment only under anaerobic conditions.

In order to be able to efficiently channel terpene biosynthetic intermediates from the ergosterol biosynthetic pathway, a SUE (sterol uptake enhancement) mutation supporting the aerobic uptake and utilization of exogenous sterol was first created (Bourot and Karst, 1995; Shianna et al., 2001). A SUE mutation is thus a yeast line that can meet all its sterol needs by an exogenous source of sterol, and therefore making the endogenous ergosterol biosynthetic pathway dispensable. The SUE mutation was then complemented by the introduction of a knockout mutation in the ERGS gene (squalene synthase) (Zhang et al., 1993), resulting in a yeast line where the MVA pathway was still operational up to the biosynthesis of FPP and hence, intermediates in the pathway (DMAPP, IPP and FPP) could be diverted to the biosynthesis of other non-essential terpene components. In order to follow and select for the desired mutant lines, the yeast lines could be monitored for farnesol (FOH) accumulation, the dephosphorylated form of farnesyl diphosphate. If the MVA pathway in the yeast line continued to operate as proposed, then one would expect carbon flux to FPP to continue. But, because the downstream utilization of FPP by squalene synthase was abolished, then the accumulating FPP would be subject to the endogenous phosphatase activity for its conversion to FOH, which could be used as an initial screen for monitoring development of the mutant yeast line. Further engineering of such a yeast line could then take advantage of the FPP, DMAPP and IPP pools for their diversion to the biosynthesis of monoterpenes (10 carbon compounds), sesquiterpenes (15 carbon compounds), diterpenes (20 carbon compounds) and triterpenes (30 carbon compounds).

Figure 6:
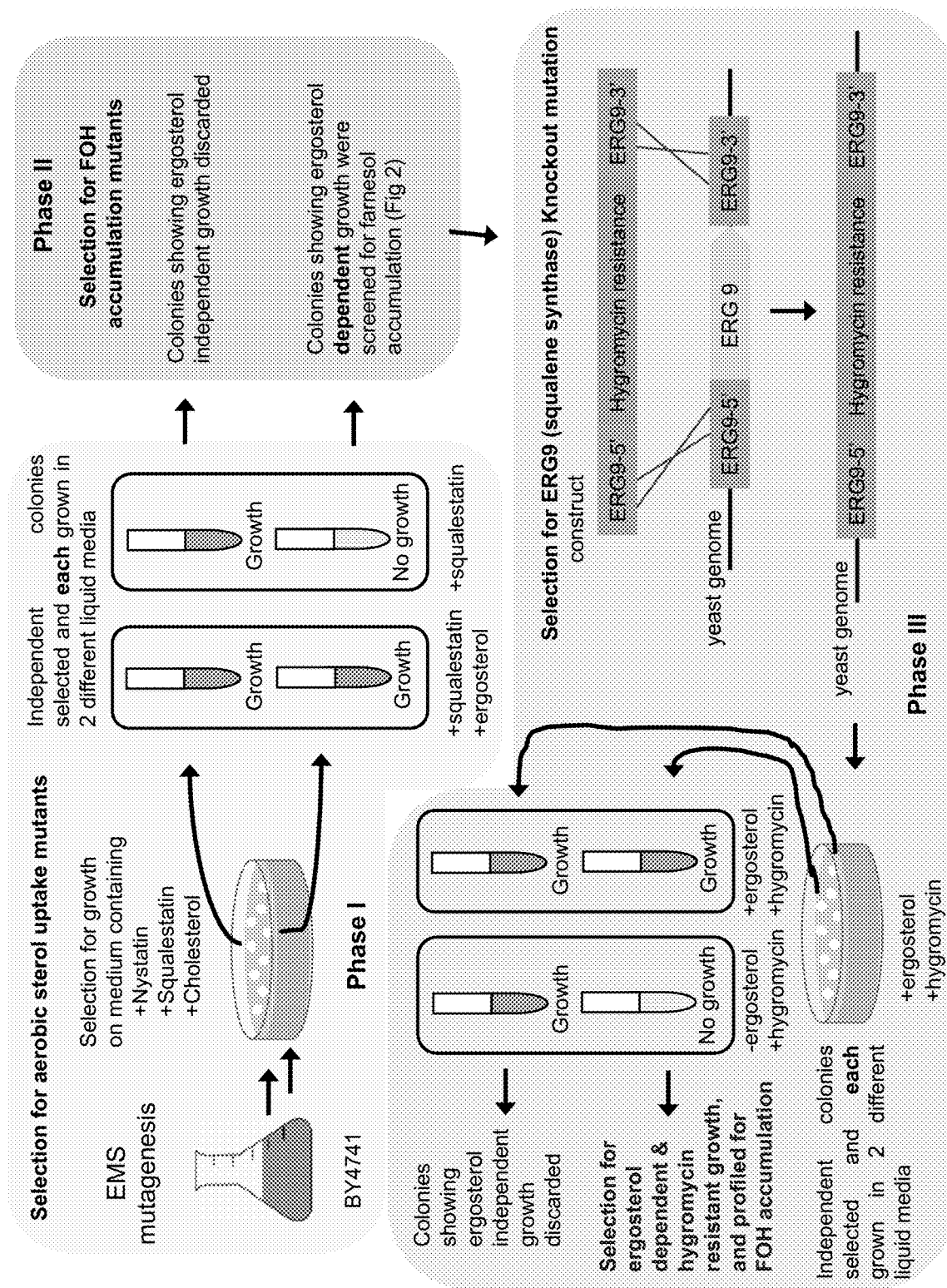
FIG. 6 is a flow diagram showing the biogenesis of modified yeast in accordance with one aspect of the present invention.

The following experiments were conducted to develop yeast with a dispensible mevalonate pathway. FIG. 6 illustrates three (3) phases in the development of a desired yeast line. In phase I, chemical mutagenesis is used to introduce SUE mutations, which are identified by selecting for yeast cells that do not have a functioning ergosterol biosynthetic pathway and can only grow in the presence of exogenous cholesterol. The SUE mutation was created by subjecting wild type yeast strain BY4741 to EMS mutagenesis (see supplemental materials and methods information for specifics) to introduce random mutations in the whole genome, followed by selection on plates containing three important selection agents: nystatin; cholesterol; and squalestatin. Nystatin binds to ergosterol in the cell membrane causing non-selective membrane permeability and leads to cell death (Silva et al., 2006). Nystatin thus selects against cells that have ergosterol in their membranes. However, yeast have an absolute requirement for sterols in order for their membranes to function properly. Hence, by having the mutagenized yeast plated in the presence of cholesterol, which nystatin cannot bind to, only yeast that can take up the exogenous cholesterol under aerobic conditions and properly incorporate the cholesterol into their membranes survive. Squalestatin is a potent inhibitor of squalene synthase and eliminates the yeast's ability to synthesize ergosterol (Bergstrom et al., 1995), thus assuring that the surviving yeast have a dispensable mevalonate pathway.

Figure 11:
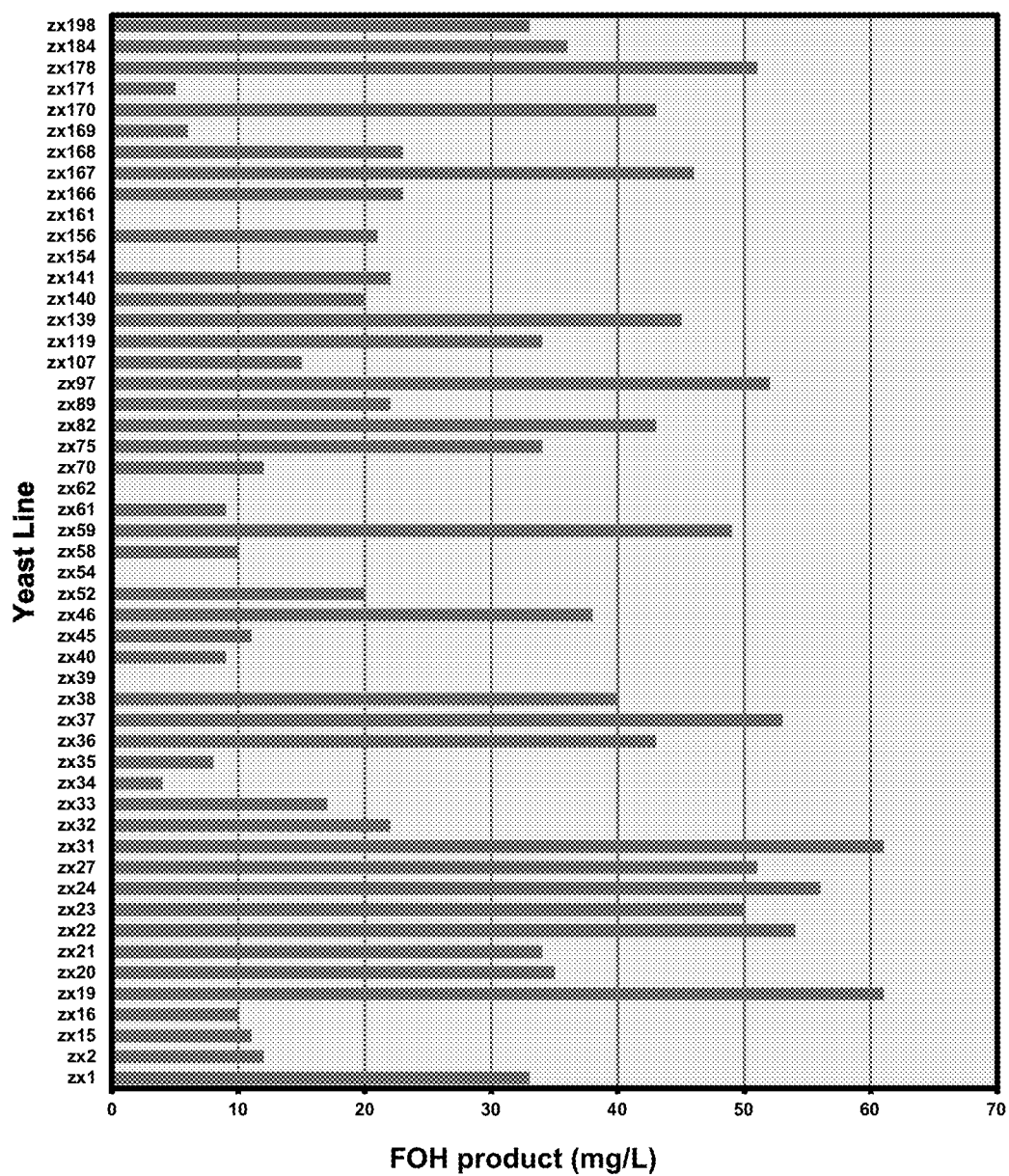
FIG. 11 is a graph showing quantitation of FOH levels in yeast lines having an exogenous sterol requirement growth.

In phase II, yeast lines demonstrating an absolute requirement for exogenous sterols for growth were chemical profiled by GC-MS (FIG. 11). Aliquots of those yeast lines exhibiting normal growth characteristics, having growth rates comparable to wild type yeast, were extracted and their chemical constituents separated by gas chromatography and identified by their mass fragmentation patterns. The parental line BY4741 does not accumulate detectable amounts of FOH under these conditions. Mutant lines accumulating 50 or more mg/ml of FOH were selected for phase III knockout mutagenesis of the squalene synthase gene, ERGS.

As shown in FIG. 11, quantitation of FOH levels in yeast lines having an exogenous sterol requirement for growth. Yeast lines were grown as test tube shake cultures with 3 ml of YPD media containing 40 µg/ml of ergosterol and 40 µg/ml of squalestatin for 6 days prior to sampling the cultures. One ml aliquots of cultures were mixed vigorously with 1 ml of acetone, then allowed to stand for 15 min. One ml of hexane containing a cedrene external standard was then added, vortexed, centrifuged in a clinical centrifuge for 5 min, and the upper hexane phase removed and concentrated to 100 µl under a nitrogen stream. One µl aliquots of the hexane extracts were then subjected to GC-MS and FOH levels quantified relative to the external standard.

The objective in phase III was to obtain a knockout mutation of the ERG 9 (squalene synthase) gene, thus assuring the dispensable nature of the endogenous mevalonate pathway for ergosterol biosynthesis. Site specific recombination was afford by appending 5' and 3' regions surrounding the native ERG9 gene onto a hygromycin selection marker gene (see supplementary materials and methods information), then introducing this linear gene construct into selected yeast lines from the phase II screening under conditions to promote site-specific, double recombination with the native ERRS gene. The knockout mutants were then selected by plating the cells in the presence of ergosterol and hygromycin. Recombination as depicted in FIG. 6 should result in the coding region of the ERG9 gene being displaced/substituted by the hygromycin resistance marker gene. Confirmation of such a substitution event was obtained by screening the genomic DNA of the selected yeast colonies for the hygromycin marker gene in proximity to genomic DNA sequences normally found 3' to the ERG9 coding region. Using genomic DNA isolated from hygromycin resistant colonies as template with a hygromycin specific primer (HphF) and a primer specific to a genomic DNA sequence found 3' to the ERG9 gene (ERG9 450DwR), a PCR amplification product of approximately 1,538 bp would be expected and is evident in the colonies so tested in FIG. 12.

Figure 12:
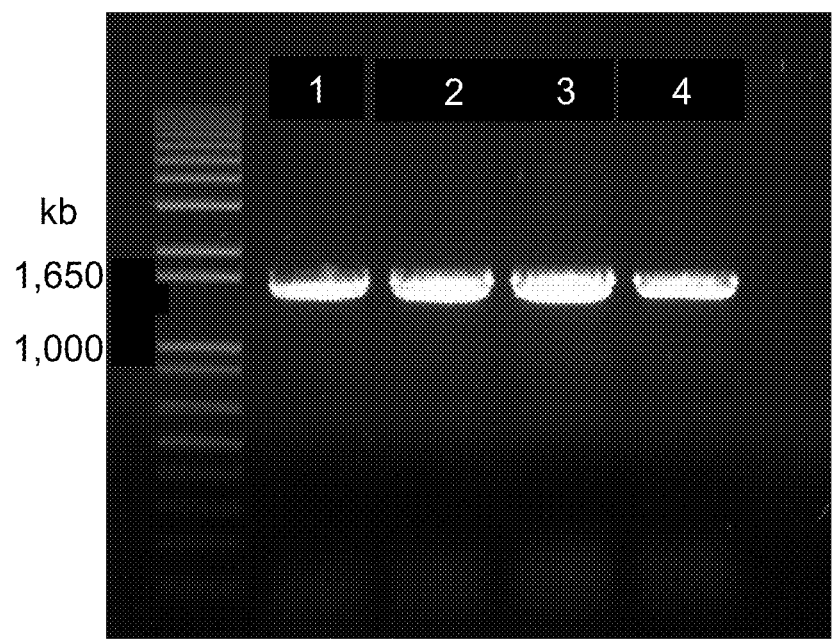
FIG. 12 is a gel confirming erg9 knockout mutation in accordance with the present invention.

In FIG. 12, PCR confirmation for the ERG9 knockout mutation include DNA isolated from four independent colonies selected for substitution of the hygromycin resistance gene for the ERG9 gene, used as PCR template with a hygromycin specific primer and a specific primer for the genomic DNA surrounding the ERG9 locus. If the HphF gene did insert and replace the ERG9 gene, the expected amplification product would be 1,538 bp. Independent colonies from each of the erg9 knockout lines were then re-evaluated for their growth in liquid media and the dispensable nature of their mevalonate pathway checked by their accumulation of FOH (FIG. 13).

Figure 13:
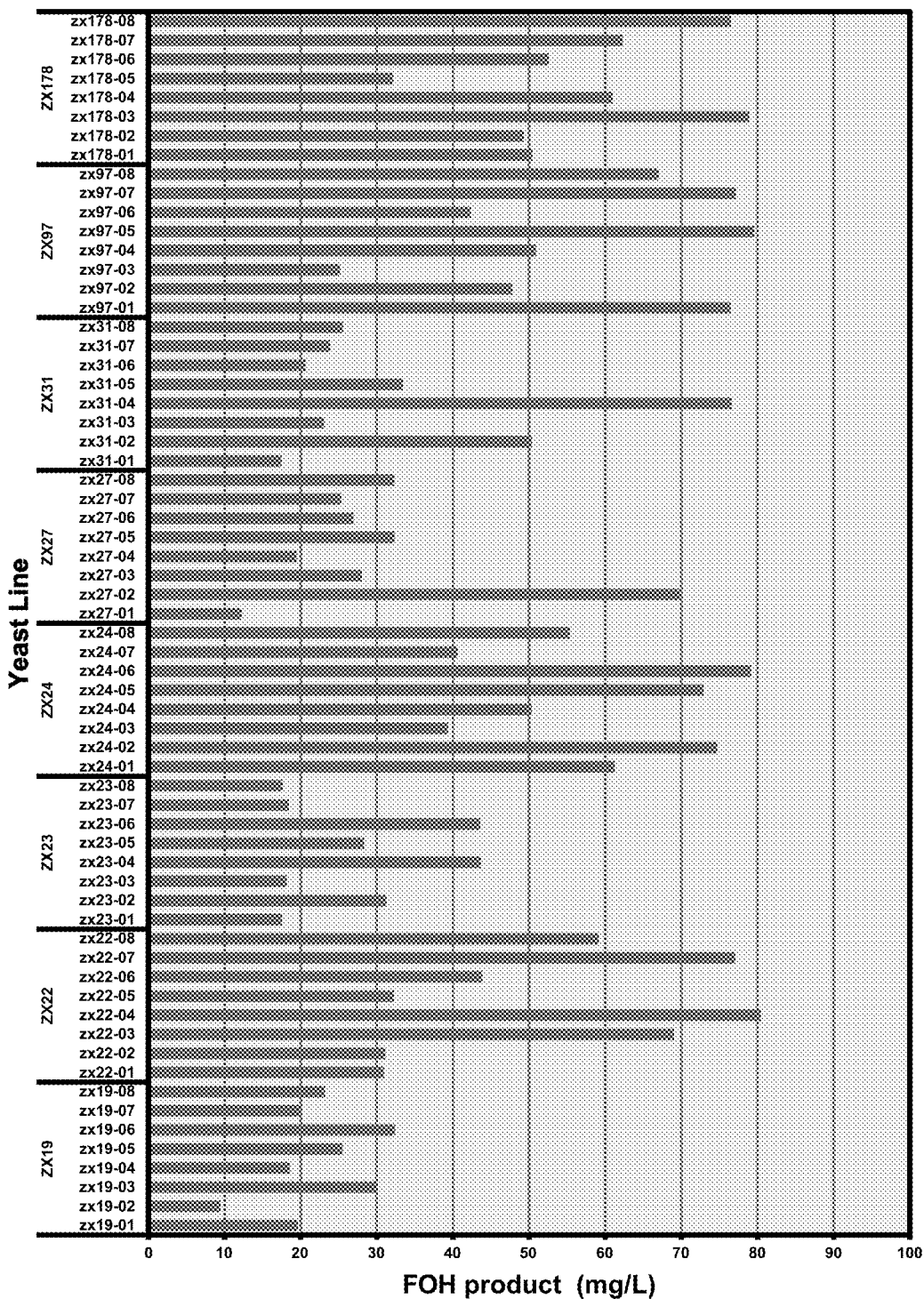
FIG. 13 is a chart showing the quantitation of FOH levels in SUE, erg9 mutant lines of yeast demonstrated to have an exogenous sterol requirement for growth and resistance to hygromycin.

As shown in FIG. 13, quantitation of FOH levels in SUE, erg9 mutant lines of yeast demonstrated to have an exogenous sterol requirement for growth and resistance to hygromycin. Cultures were grown in 3 ml test tube cultures of SCE media supplemented with histidine, leucine, uracil, tryptophan and methionine for 6 days before extracting and quantifying their FOH levels by GC-MS as described in FIG. 11.

Qualification of a New Mutant Yeast Strain for its Utility to Produce a Desired Terpene Compound.

Figure 7:
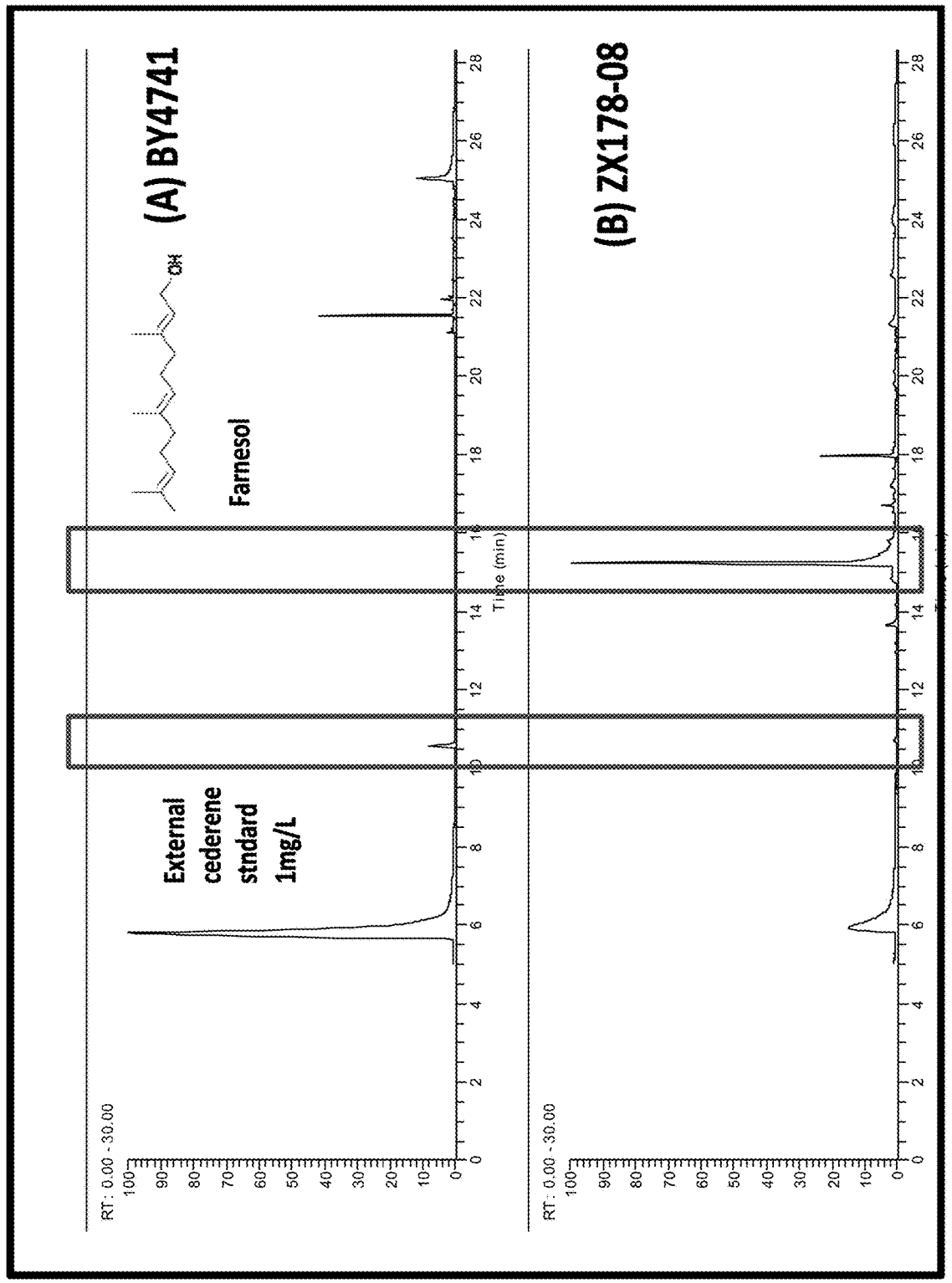
FIG. 7 is a graph showing metabolism of two strains BY4741(A) and ZX178-08(B).

Nine of the yeast lines harboring a SUE mutation and having the native ERG8 gene deleted were evaluated indirectly for the available of terpene biosynthetic intermediates, and specifically FPP, to support sesquiterpene biosynthesis in comparison to the parental strain BY4741 (FIG. 7). *Hyoscyamus* premnaspirodiene synthase (HPS), a catalytically active sesquiterpene synthase first isolated from *Hyoscyamus muticus*, was chosen for this evaluation because HPS has been characterized for its expression in bacteria (Mathis et al., 1997) and in yeast (Takahashi et al., 2007). An appropriate HPS gene expression vector was engineered into the indicated yeast lines and the subsequent transformants screened for premnaspirodiene accumulation when the yeast were grown as 30 ml shake flask cultures with SCE media containing leucine, tryptophan, uracil, and methionine for 12 days at 23° C. Yeast line ZX178-08 accumulated the highest level of premnaspirodiene, up to 114±26 mg/L, with FOH levels of 23.6±14.5 mg/L. In comparison, the parental line BY4741 accumulated 10 times less premnaspirodiene, 10.94±3.12 mg/L, with no farnesol accumulation detected.

Figure 9:
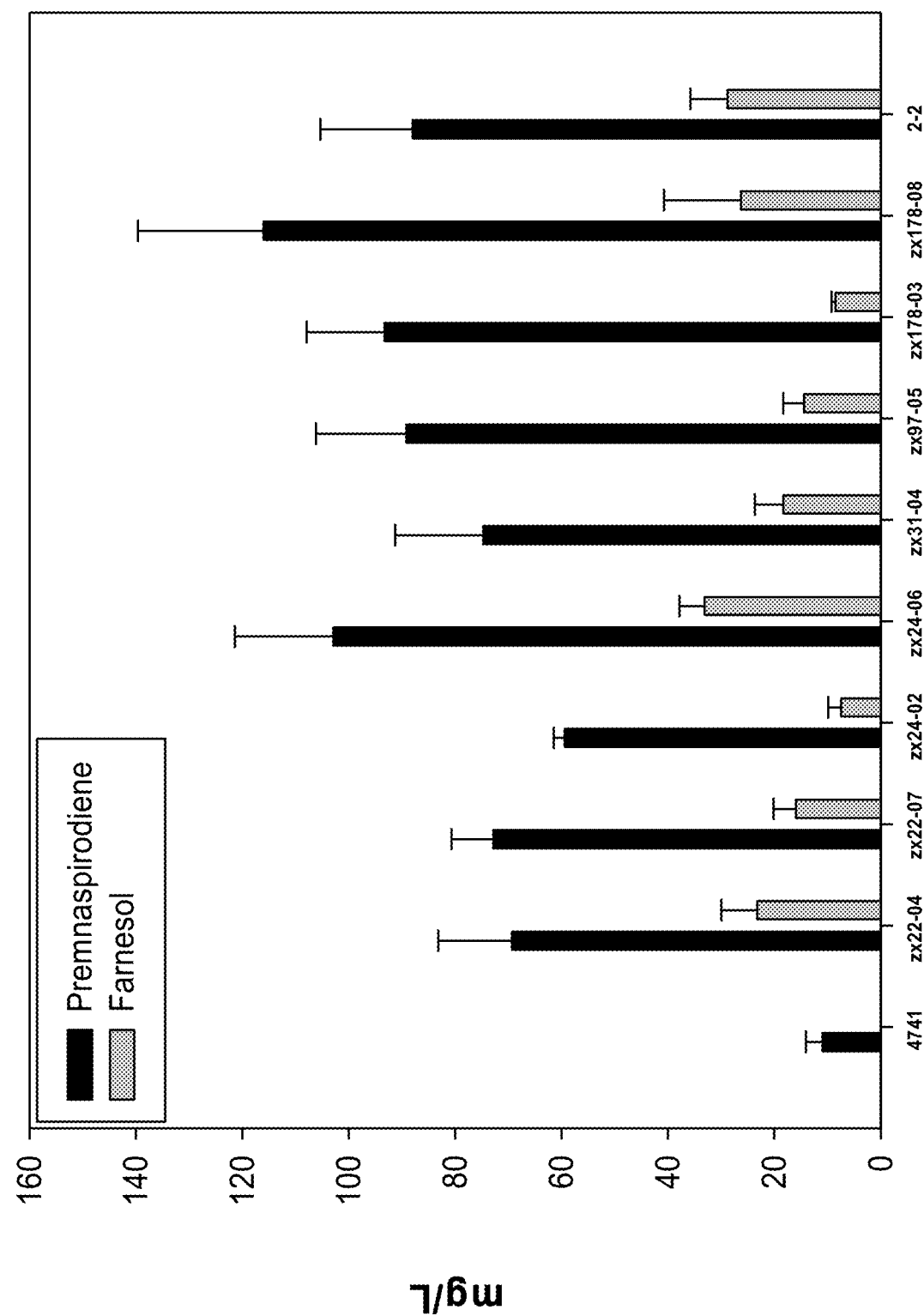
FIG. 9 shows how the yeast lines developed as outlined in FIG. 8 in comparison to the starting yeast line 4741 were chemically profiled for their terpene biosynthetic capacities.
Figure 10:
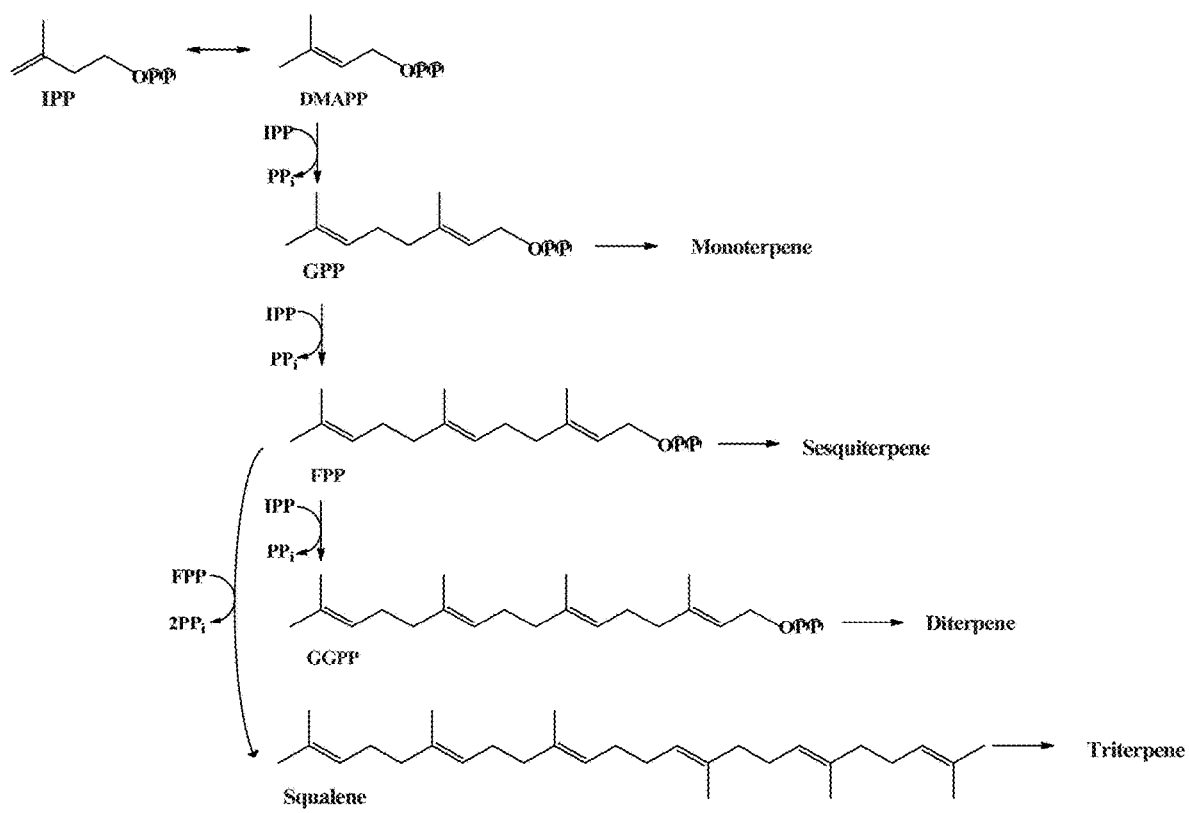
FIG. 10 is a chart showing the production of various compounds of different strains in accordance with the present invention.

FIG. 9 shows a comparison of terpene accumulation levels in yeast lines (ZX series) developed as terpene production platforms. Each of the ZX cell lines as well as the wild type parental line (BY4741) were independently transformed with an expression vector harboring the *Hyoscyamus* premnaspirodiene synthase gene. The yeast lines were then grown for 12 days prior to chemically profiling them for their cell constituents by GC-MS and quantifying the levels of premnaspirodiene and farnesol found in each.

The following experiments methods and procedures provide additional background with regard to the method for producing terpene platforms in yeast and the resulting yeast produced.

Chemical and Media Preparations

All chemical reagents were obtained from Sigma-Aldrich (St. Louis, Mo.), BD Bioscience (Franklin Lakes, N.J.), or Fisher Scientific (Chicago, Ill.), while reagents for molecular manipulations were from Stratagene (San Diego, Calif.), Takara (Shiga, Japan), Invitrogen (San Diego, Calif.), and New England Biolab (Ipswich, Mass.).

Bacteria and yeast were grown using standard culture practices. YPD media for growing yeast without selection consisted of 1% Bactoyeast extract, 2% Bacto-peptone, and 2% glucose (or 0.5% glucose for select experiments). YPDE media was YPD media supplemented with ergosterol (40 mg/L) for ergosterol dependent lines. YPDNCS media for the SUE mutation screening was YPD media supplement with 40 mg/L Nystatin, 40 mg/L cholesterol and 40 mg/L squalestatin. YPDSE media was YPD media supplement with 40 mg/L squalestatin and 40 mg/L ergosterol. Minimal media, SCE (pH 5.3), contained 0.67% Bacto-yeast nitrogen base (without amino acids), 2% dextrose, 0.6% succinic acid, 0.14% Sigma yeast dropout solution (-his,-leu,-ura,-trp), uracil (300 mg/L), L-tryptophan (150 mg/L), L-histidine (250 mg/L), L-methionine (200 mg/L), L-leucine (1 g/L) and 40 mg/L ergosterol. Cholesterol and ergostrol stocks were 10 mg/mL in 50% Triton X-100, 50% ethanol and kept at −20° C. Selection media was prepared similarly except without supplementing the media with the indicated reagent based on the yeast auxotrophic makers. All solid media plates were prepared with 2% Bacto-Agar.

Ethyl Methane-Sulfonate (EMS) Mutagenesis

Strain BY4741 (MATa;his3A1;leu2A0;met15A0;ura3A0) (Janke et al., 2004) was used as the parental yeast line. BY4741 cells were incubated overnight at 30° C. in 5 ml YPD medium with shaking at 200 rpm, and used to establish a 200 ml YPD shake flask culture. When the yeast culture OD600 reached approximately 1.0, the cells were spun down by centrifugation (10 min at 4,000×g), and washed twice with 20 ml 0.1M sodium phosphate buffer, pH7.0. Cells were concentrated by centrifugation again, re-suspended in 1 ml 0.1M sodium phosphate buffer, transferred to a 14 ml FALCON culture tubes, treated with 300 pi EMS (1.2 g/ml, Sigma), followed by incubation at 30° C. for 1 hour with shaking. To stop the mutagenesis, 8 ml of sterile 5% sodium thiosulfate (Fisher) were added to yeast cells by inactive EMS. Cells were pelleted, washed with 8 ml sterile water, concentrated by centrifugation, re-suspended in 1 ml sterile water and 100 pl aliquots plated onto YPD-NCS agar plate (YPD plus 50 mg/L cholesterol, 50 mg/L nystatin, 50 mg/L squalesatin, 2% Bacto-agar). In some experiments, the washed cells were resuspend in 1 ml YPDE liquid media for recovery overnight before plating on YPD-NCS agar medium. The cultures were incubated for up to 2 weeks at 30° C. until distinct colonies became visible.

Yeast Transformation and Culture Performance

Yeast strains were transformed with the respective vector constructs using the FROZEN-EZ Yeast Transformation II Kit (Zymo Research, Orange, Calif.) according to the manufacturer's recommendations. About 1 pg of plasmid or about 5 pg of linearized DNA was used per transformation and followed by selection on agar plates of SCE medium lacking specified amino acids for the auxotrophic markers or YPDE containing 300 mg/L hygromycin B for screening for erg9 knockout at 30° C. Variable numbers of independent colonies were subsequently picked and used to start 3 ml cultures in minimal media to characterize their terpene production capacities. Aliquots of these cultures were analyzed for terpene production after 6 days of incubation at 30° C. with shaking by GC-MS. Cultures exhibiting the highest terpene production levels were chosen for further studies and archived as glycerol stocks at −80° C. Selected lines were characterized for cell growth and terpene production using 30 mL shake flask cultures. Starter cultures grown to saturation in minimal media were inoculated into 30 ml SCE media and 1 mL aliquots withdrawn at every other day intervals for 10-15 days. Cell growth was monitored as the change in optical density at 600 nm every two days, using appropriate dilutions for cultures at later stages of growth. Terpene production was determined by GC-MS similar to the initial screening method.

GC-MS Detection and Quantification of Terpenes

To determine terpene accumulation levels, aliquots of cultures grown for 6 to 12 days were extracted with hexane and aliquots evaluated by GC-MS. In general, to 1 volume of culture, 1 volume of acetone was added and mixed vigorously for 3 to 5 min to lyre the cells. The sample was then allowed to incubate at room temperature for 10 min before adding 1 volume of hexane containing a known amount of cedrene external standard. The mixture was again mixed vigorously, then centrifuged in a clinical centrifuge for 5 min at maximum speed. The upper organic layer was collected and when necessary, concentrated under a N2 stream to 1/10 the original volume. An aliquot of the organic phase (1 µl) was then analyzed by GC-MS with a Varian CP-3800 GC coupled to a Varian Saturn 2200 MS/MS (Varian Medical Systems) using a Supelco SLB-5 ms fused silica capillary column (30 m×0.25 mm×0.25 pm film thickness, Supelco). The initial oven temperature was set at 70° C. for 1 min, ramped to 200° C. at 8° C./min, and then ramped to 300° C. at 20° C./min and held for 5 min more. Farnesol and premnaspirodiene levels were calculated relative to the cedrene external standard.

Construction of the Squalene Synthase (ERG9) Knockout Mutation

The primers ERG9PS1 and ERG-250downS2 were used to amplify the hygromycin resistance gene, hphNT1, from the PFA6-hph-NT1 vector (Janke et al., 2004), and at the same time add DNA sequences homologous to regions surrounding the ERG9 gene in the yeast genome. These primers are flanked by 42 nucleotide sequences (underlined) homologous to DNA sequences found 250 base pairs 5' (upstream) and 3' (downstream), respectively, of the ERG9 gene found in the yeast genome. The purified PCR fragment was transformed into various yeast lines identified for their ability to accumulate farnesol (FIG. 11) and grown in 2 ml of YPDE media for an additional 6 hours before being plated on YPDE hygromycin (300 mg/L) agar plates at 28° C. Independent single colonies were picked for ergosterol dependent test, PCR confirmation of recombination with hphF and ERG9 450DWR primer, as well as farnesol production analysis. The recombination sequence was further confirmed by DNA sequencing of a corresponding PCR amplification product.

Expression of the HPS Gene in Yeast

The yeast GPD promoter (Pgpd) was amplified from the PYM-N14 plasmid described by Janke et al. (2004) using the primers GPD-BamHIF and GPD-NotIR primers and inserted into the pESC-His vector digested with BamHI and NotI to replace the original GAL1/10 promoters. The resulting plasmid was named pESC-His-gpd. The HPS gene was cloned into NotI and SpeI sites of pESC-His-gpd to obtain the yeast expression vector pESC-His-gpd-HPS as previously by Takahashi et al. (2007). Yeast lines transformed with this construct were then evaluated for their production of the sesquiterpene premnaspirodiene as a measure of the available of intermediates of the mevalonate biosynthetic pathway for the biosynthesis of new terpenes.

Figure 14:
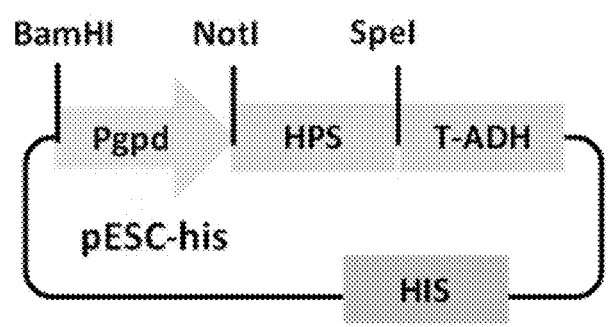
FIG. 14 is a flow chart showing constructs used for evaluate yeast sesquiterpene productions.

Referring to FIG. 14, a yeast expression vector was designed for a strong, consecutive expression of the sesquiterpene synthase HPS gene directed by the gpd promoter (Pgpd) and termination provided by the ADH terminator sequence (ADHterm).

Figure 15:
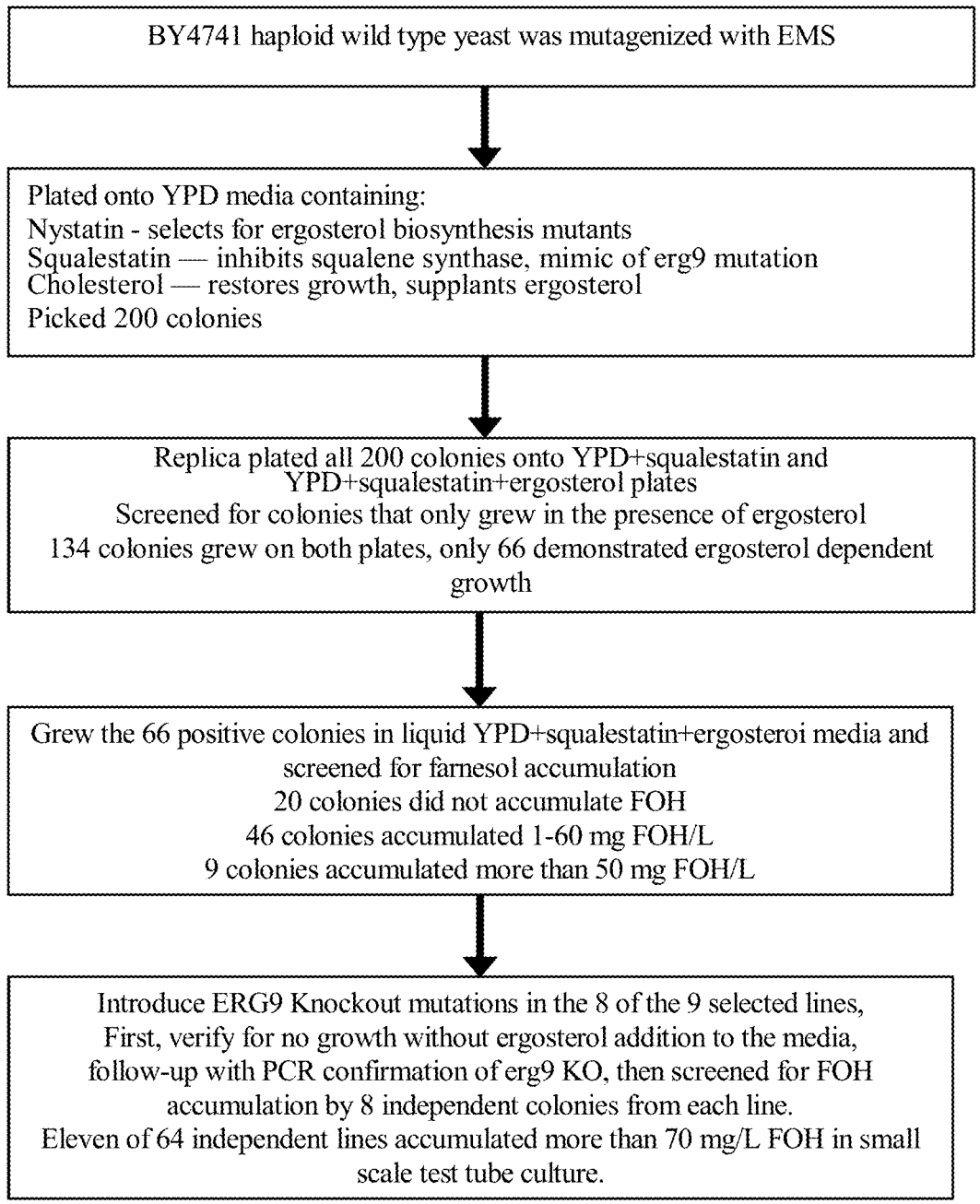
FIG. 15 is a flow diagram showing the steps in the development of yeast.

In FIG. 15, steps are shown for the development of yeast having a desirable mevalonate biosynthetic pathway and number of colonies screened at each stage.

Figure 8:
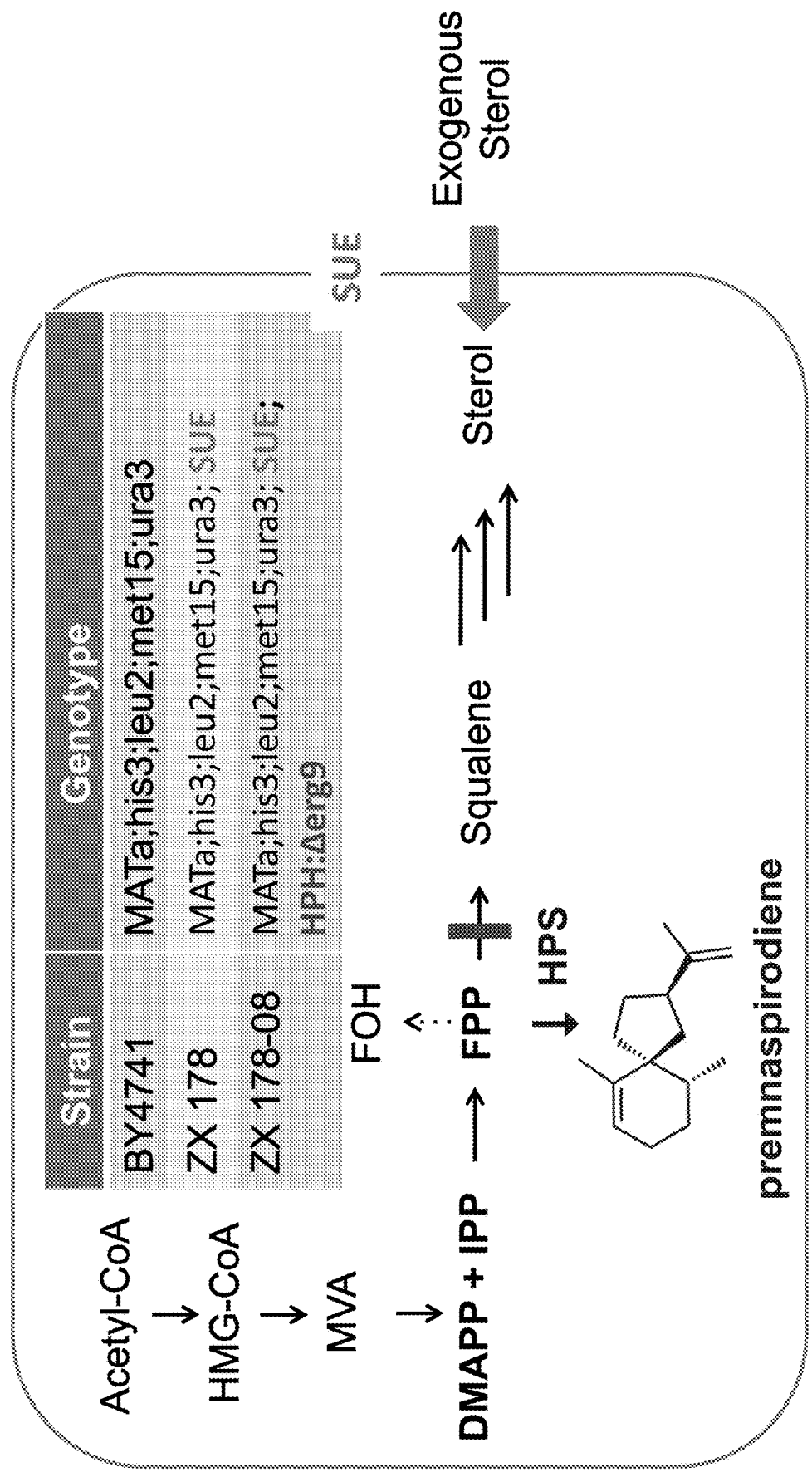
FIG. 8 illustrates how yeast strains produced in accordance with the present method can be used for producing specific chemicals.

FIG. 8 shows FOH accumulation in a yeast line (178-08) selected for a dispensable mevalonate biosynthetic pathway in comparison to that accumulating in the parental line (BY4741) used to generate the new mutant yeast lines. GC-MS chromatograph of hexane extracts were prepared from the wild type and engineered yeast lines. The top of FIG. 8, for (A) BY4741, shows no farnesol accumulated in parental yeast. In the bottom part of FIG. 8, (B) ZX178-08, over 100 mg of FOH/L accumulated in the newly developed yeast line, as quantified on the basis of a cedrene external standard.

The following table shows primers used in various molecular manipulations described in the present disclosure.

| Primer Name | Primer sequence | Sequence Identifier |
|---|---|---|
| ERG9pS1 | GTACATTTCATAGCCCATCTTCAAC AACAATACCGACTTA | SEQ ID NO: 1 |
|  | CCCGTACGCTGCAGGTCGAC | SEQ ID NO: 2 |
| ERG9 250dw52 | CAGATTGACGGAGAGAGGGCCACAT TGTTTGTCGGCAA | SEQ ID NO: 3 |
|  | TAAATCGATGAATTCGAGCTCG | SEQ ID NO: 4 |
| Hph F | ATGGGTAAAAAGCCTGAACTCA | SEQ ID NO: 5 |
| Hph R | TTATTCCTTTGCCCTCGGACGAG | SEQ ID NO: 6 |
| ERG9 450c1Wr | AGATGCTAGTCAATGGCAGAAG | SEQ ID NO: 7 |
| ERG9p300upF | TGCTTACACAGAGTGAACCTGC | SEQ ID NO: 8 |
| ERG9 300R | CTCGTGGAAGTGACGCAAC | SEQ ID NO: 9 |
| HPS Not1 F | gggGCGGCCGCaAAAACA atggcccagctatagtgatgag | SEQ ID NO: 10 |
| HPS SpeIR | gACTAGT tcaaatatcaatagaatccacc | SEQ ID NO: 11 |
| pGPD-BamHI F | cgGGATCCagtttatcattatca atactcgcc | SEQ ID NO: 12 |
| pGPD-NotIR | gggGCGGCCGCgagctcagttta tcattatc | SEQ ID NO: 13 |

It will be understood that various details of the presently disclosed subject matter can be changed without departing from the scope of the subject matter disclosed herein. Furthermore, the foregoing description is for the purpose of illustration only, and not for the purpose of limitation.

The present application includes a sequence listing:
Name: 13177N_1860CO_SequenceListing.txt
Date Created: Nov. 5, 2020
Size: 6 KB

REFERENCES

Numerous references have been cited throughout this disclosure including the following. All are incorporated by reference.

Asadollahi M A, Maury J, Moller K, Nielsen K F, Schalk M, Clark A, Nielsen J (2008) Production of plant sesquiterpenes in *Saccharomyces cerevisiae*: Effect of ERGS repression on sesquiterpene biosynthesis. Biotechnology and Bioengineering 99: 666-677

Asadollahi M A, Maury J, Schalk M, Clark A, Nielsen J (2010) Enhancement of farnesyl diphosphate pool as direct precursor of sesquiterpenes through metabolic engineering of the mevalonate pathway in *Saccharomyces cerevisiae*. Biotechnology and Bioengineering 106: 86-96

Bedoukian P E (1983) Perfumery and flavour materials. Perfumer & Flavorist 8: 1, 3-6

Bergstrom J D, Dufresne C, Bills G F, Nallinomstead M, Byrne K (1995) Discovery, biosynthesis, and mechanism of action of the zaragozic acids potent inhibitors of squalene synthase. Annual Review of Microbiology 49: 607-639

Bhilwade H N, Tatewaki N, Nishida H, Konishi T (2010) Squalene as novel food factor. Current Pharmaceutical Biotechnology 11: 875-880

Bourot S, Karst F (1995) Isolation and characterization of the *saccharomyces-cerevisiae* sut1 gene involved in sterol uptake. Gene 165: 97-102 Buckingham J (2003) Dictionary of Natural Products. Chapman & Hall/CRC Chemical Database Casida J E (2009) Pest toxicology: The primary mechanisms of pesticide action. Chemical Research in Toxicology 22: 609-619

Fischer M J C, Meyer S, Claude! P, Bergdoll M, Karst F (2011) Metabolic engineering of monoterpene synthesis in yeast. Biotechnology and Bioengineering 108: 1883-1892

Huang Z-R, Lin Y-K, Fang J-Y (2009) Biological and pharmacological activities of squalene and related compounds: potential uses in cosmetic dermatology. Molecules 14: 540-554

Janke C, Magiera M M, Rathfelder N, Taxis C, Reber 5, Maekawa H, Moreno-Borchart A, Doenges G, Schwob E, Schiebel E, Knop M (2004) A versatile toolbox for PCR-based tagging of yeast genes: new fluorescent proteins, more markers and promoter substitution cassettes. Yeast 21: 947-962

Keasling J (2009) Synthetic biology in pursuit of inexpensive, effective, antimalarial drugs. Biosocieties 4: 275-282

Kirby J, Romanini D W, Paradise E M, Keasling J D (2008) Engineering triterpene production in *Saccharomyces cerevisiae*-beta-amyrin synthase from *Artemisia annua*. Febs Journal 275: 1852-1859

Maertens J A (2004) History of the development of azole derivatives. Clinical Microbiology and Infection 10: 1-10

Martin V J J, Pitera D J, Withers S T, Newman J D, Keasling J D (2003) Engineering a mevalonate pathway in *Escherichia coli* for production of terpenoids. Nature Biotechnology 21: 796-802

Mathis J R, Back K, Starks C, Noel J, Poulter C D, Chappell J (1997) Pre-steady-state study of recombinant sesquiterpene cyclases. Biochemistry 36: 8340-8348

Nicolaou K C, Yang Z, Liu J J, Ueno H, Nantermet P G, Guy R K, Claiborne C F, Renaud J, Couladouros E A, Paulvannan K, Sorensen E J (1994) Total synthesis of taxol. Nature 367: 630-634

Reddy L H, Couvreur P (2009) Squalene: A natural triterpene for use in disease management and therapy. Advanced Drug Delivery Reviews 61: 14121426

Seki H, Ohyama K, Sawal S, Mizutani M, Ohnishi T, Sudo H, Akashi T, Aoki T, Saito K, Muranaka T (2008) Licorice beta-amyrin 11-oxidase, a cytochrome P450 with a key role in the biosynthesis of the triterpene sweetener glycyrrhizin. Proceedings of the National Academy of Sciences of the United States of America 105: 14204-14209

Shianna K V, Dotson W D, Tove S, Parks L W (2001) Identification of a UPC2 homolog in *Saccharomyces cerevisiae* and its involvement in aerobic sterol uptake. Journal of Bacteriology 183: 830-834

Silva L, Coutinho A, Fedorov A, Prieto M (2006) Competitive binding of cholesterol and ergosterol to the polyene antibiotic nystatin. A fluorescence study. Biophysical Journal 90: 3625-3631

Takahashi S, Yeo Y, Greenhagen B T, McMullin T, Song L, Maurina-Brunker J, Rosson R, Noel J P, Chappell J (2007) Metabolic engineering of sesquiterpene metabolism in yeast. Biotechnology and Bioengineering 97: 170-181

Tu Y (2011) The discovery of artemisinin (qinghaosu) and gifts from Chinese medicine. Nature Medicine 17: 1217-1220

Wall M E, Wani M C (1995) Paclitaxel—from discovery to clinic. In GICTTOIVDM Georg, ed, Taxane Anticancer Agents: Basic Science and Current Status, Vol 583, pp 18-30

Wu S Q, Schalk M, Clark A, Miles R B, Coates R, Chappell J (2006) Redirection of cytosolic or plastidic isoprenoid precursors elevates terpene production in plants. Nature Biotechnology 24: 1441-1447

Zhang D L, Jennings S M, Robinson G W, Poulter C D (1993) Yeast squalene synthase—expression, purification, and characterization of soluble recombinant enzyme. Archives of Biochemistry and Biophysics 304: 133143

The invention claimed is:

1. A method for generating terpene producing yeast cell lines, the method comprising:

combining yeast with a chemical mutagenesis agent to induce mutations in the yeast to generate chemically mutated yeast;

selecting chemically mutated yeast which grows in the presence of nystatin, squalestatin and cholesterol, followed by selecting for ergosterol dependent growth; and subjecting the ergosterol dependent growth yeast to an erg9 knockout mutation, to thereby produce ergosterol dependent growth/erg9 knockout mutation yeast cell lines.

* * * * *

SEQUENCE LISTING

```
<160> NUMBER OF SEQ ID NOS: 13

<210> SEQ ID NO 1
<211> LENGTH: 40
<212> TYPE: DNA
<213> ORGANISM: Artificial Sequence
<220> FEATURE:
<223> OTHER INFORMATION: primer sequence

<400> SEQUENCE: 1
```

```
gtacatttca tagcccatct tcaacaacaa taccgactta                              40

<210> SEQ ID NO 2
<211> LENGTH: 20
<212> TYPE: DNA
<213> ORGANISM: Artificial Sequence
<220> FEATURE:
<223> OTHER INFORMATION: primer sequence

<400> SEQUENCE: 2
cccgtacgct gcaggtcgac                                                   20

<210> SEQ ID NO 3
<211> LENGTH: 38
<212> TYPE: DNA
<213> ORGANISM: Artificial Sequence
<220> FEATURE:
<223> OTHER INFORMATION: primer sequence

<400> SEQUENCE: 3
cagattgacg gagagagggc cacattgttt gtcggcaa                               38

<210> SEQ ID NO 4
<211> LENGTH: 22
<212> TYPE: DNA
<213> ORGANISM: Artificial Sequence
<220> FEATURE:
<223> OTHER INFORMATION: primer sequence

<400> SEQUENCE: 4
taaatcgatg aattcgagct cg                                                22

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
atgggtaaaa agcctgaact ca                                                22

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
ttattccttt gccctcggac gag                                               23

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
agatgctagt caatggcaga ag                                                22

<210> SEQ ID NO 8
<211> LENGTH: 22
<212> TYPE: DNA
```

```
<213> ORGANISM: Artificial Sequence
<220> FEATURE:
<223> OTHER INFORMATION: primer

<400> SEQUENCE: 8
tgcttacaca gagtgaacct gc                                              22

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
ctcgtggaag tgacgcaac                                                  19

<210> SEQ ID NO 10
<211> LENGTH: 41
<212> TYPE: DNA
<213> ORGANISM: Artificial Sequence
<220> FEATURE:
<223> OTHER INFORMATION: primer

<400> SEQUENCE: 10
ggggcggccg caaaaacaat ggccccagct atagtgatga g                         41

<210> SEQ ID NO 11
<211> LENGTH: 29
<212> TYPE: DNA
<213> ORGANISM: Artificial Sequence
<220> FEATURE:
<223> OTHER INFORMATION: primer

<400> SEQUENCE: 11
gactagttca aatatcaata gaatccacc                                       29

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
cgggatccag tttatcatta tcaatactcg cc                                   32

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
ggggcggccg cgagctcagt ttatcattat c                                    31
```